United States Patent [19]

Hou

[11] Patent Number: 4,488,969

[45] Date of Patent: Dec. 18, 1984

[54] FIBROUS MEDIA CONTAINING MILLIMICRON-SIZED PARTICULATES

[75] Inventor: Kenneth C. Hou, San Antonio, Tex.

[73] Assignee: AMF Incorporated, White Plains, N.Y.

[21] Appl. No.: 558,453

[22] Filed: Dec. 6, 1983

Related U.S. Application Data

[62] Division of Ser. No. 347,360, Feb. 9, 1982.

[51] Int. Cl.³ .............................................. B01D 15/00
[52] U.S. Cl. .................................. 210/679; 210/692; 210/927
[58] Field of Search ............... 210/679, 691, 692, 908, 210/927

[56] References Cited

U.S. PATENT DOCUMENTS

| | | | |
|---|---|---|---|
| 3,959,128 | 5/1976 | Harris | 210/692 |
| 4,168,300 | 9/1979 | Andersson et al. | 210/679 |
| 4,381,239 | 4/1983 | Chibata et al. | 210/679 |
| 4,411,795 | 10/1983 | Olson | 210/908 |

*Primary Examiner*—Ivars Cintins
*Attorney, Agent, or Firm*—David E. Dougherty; Michael E. Zall

[57] ABSTRACT

A self-supporting fibrous matrix containing immobilized therein at least about 5% by weight of microparticulate, with an average diameter less than 1 micron, preferably fumed silica, or alumina, and flocculating amounts of an organic polycationic resin and an organic polyanionic resin, is useful for fluid treatment and filtration processes, especially delipidization and depyrogenation of fluids such as serum.

15 Claims, 5 Drawing Figures

FIBROUS MEDIA CONTAINING MILLIMICRON-SIZED PARTICULATES

This is a division, of application Ser. No. 347,360, filed Feb. 9, 1982.

BACKGROUND OF THE INVENTION

1. Field of the Invention

The present invention relates to fibrous media containing millimicron sized particulates, especially media containing fumed silica or fumed alumina.

2. Brief Description of the Prior Art

The technique of flocculating negatively charged filter aid particulates or adsorbents and fibers, by means of positively charged polymers is a common practice in the production of filtration media.

For example, Malcolm, U.S. Pat. No. 3,647,684 describes a felted fibrous matrix containing silicic acid (hydrated silica) interdispersed therein, useful for thin layer chromatography wherein the silicic acid has particle sizes within 1 to 10 microns, and which contains a cationic material in concentrations no higher than 1.5%. Ostreicher, U.S. Pat. Nos. 4,007,113 and 4,007,114 describes a matrix of self-bonding fibers containing interdispersed therein a particulate filter material, the surface of which is modified with an organic colloid. Additional patents relating to fibrous media containing interdispersed particulate material are: Pall et al, U.S. Pat. No. 3,573,158, Leifield, U.S. Pat. No. 3,455,818 and Pall et al, U.S. Pat. No. 3,238,056.

The application of positive charge flocculation techniques for the formation of specialized and improved media has also been described in commonly assigned copending U.S. patent applications Ser. No. 164,797 filed May 30, 1980, Ser. No. 147,975 filed May 8, 1980, now U.S. Pat. No. 4,305,782, and Ser. No. 123,467 filed Feb. 21, 1980, now U.S. Pat. No. 4,309,247, which are herein incorporated by reference.

The porous filter media described in these applications are comprised of fiber-particulate and fiber-fiber mixtures, with cationic charge modifiers serving as charge modifiers, wet strength providers and also as flocculating or dispersion agents in the forming slurry system.

The mixtures are formed dynamically into sheets by vacuum felting from an aqueous slurry, and subsequently drying the finished sheets as the final product. The rate of production of such porous filter media is governed by the porosity of the sheets to be produced. A highly open filter media comprising particle sizes of 50 microns or larger requires only a few seconds to be felted, whereas a tight media utilizing particle sizes of 1–2 microns or smaller would require more than 5 minutes to be felted. Sometimes, media containing the finest grades of particulate additives cannot be felted at all due to improper flocculation. Therefore, it is impossible to form a fibrous media with adsorbent particles less than 1 micron by current techniques. Moreover, the retention of such small size particles in the matrix structure is a serious problem. Most of them are lost to the water drainage during felting.

The limitations and drawbacks involved in current fibrous media manufacturing processes can be understood from the following method of formation. The application of vacuum for the formation of fibrous media is predominantly a hydromechanical process. A slurry containing all the components drains through a 100 mesh wire screen perpendicular to the plane of the screen, and drags all the components with its movement during felting. Large fibers which have the largest surface area in contact with water of any of the components in the slurry, receive the strongest viscous drag force and settle ahead of others to form a bottom fibrous network. This process provides a self-adjusting mechanism for uniform distribution of particles and fibers in the fibrous structure, based upon the fact that the drainage flow always seeks the path of least resistance. While the large fibers are preferentially retained during the initial deposition, smaller fiber fragments tend to migrate through the fiber mat of long fibers and become lodged in the interfiber holes, to provide a coherent mat structure for adsorbent particles to settle in. Continuous application of vacuum after sheet forming, induces mat compaction. The compacting force exerted by the high vacuum, further squeezes water molecules out of the wet pad, and forces adsorbent particles closer together to form a pad with definite porosity.

The above described method, however, is applicable only to particles larger than about 1 micron. In the case of particle sizes less than 1 micron, especially millimicron sized ones, such particles either fail to be retained by the fiber matrix, or fail to be further felted after forming a thin layer of compact particulate.

In particular, the formation of fibrous mats with a high load of millimicron sized particulate (e.g., higher than about 30% by weight) and with high porosity is near to impossible using the felting techniques of the prior art. Among the millimicron sized particles of great interest for commercial chemical and biochemical applications is fumed silica.

The removal of lipids through adsorption on silica is a common practice in chemistry and biochemistry. See e.g. Stephan, U.S. Pat. No. 3,686,395 and commonly asigned copending U.S. patent application Ser. No. 238,686 filed Feb. 27, 1981 to Carpenter and Cone entitled TISSUE CULTURE MEDIA. The efficiency of lipid removal by silica differs with the process by which the silica is made. Silicas precipitated from the vapor phase are better lipid removal agents than those precipitated from sodium silicate solutions. Typical commercial products of silicas made from vapor phase are Cab-O-Sil ®, Aerosil ® (Degussa) or Sipernet 22S ®. These products exist in minute particles having average diameters from 7 to 18 millimicrons (or nano-meters). They are produced by the hydrolysis of silicon tetrachloride vapor in a flame of hydrogen and oxygen. At a flame temperature of 1270° K. the vapor pressure of $SiO_2$ is only $10^{-8}$ Torr, so that there is a very high supersaturation, resulting in large numbers of small nuclei forming silica spheres with diameters ranging from 7 to 18 millimicrons on the average. These molten spheres, termed primary particles, collide and fuse with one another to form branched, three dimensional, chain-like aggregates. During the hydration of fumed silica, hydroxyl groups become attached to some of the silicon atoms on the particle surfaces. This makes the fumed silica surface hydrophilic, and capable of hydrogen bonding with other molecules.

Fumed silica is fluffy and low in density (approximately 2 lbs. per cu. ft.). Even a small amount of fumed silica packed in a column will create extremely high pressures upon contact with buffer solutions, due to the formation of a three dimensional network among the particles, with water molecules functioning as bridges. When prior art methods of dispersal of particulates in fibrous media are applied to fumed silica, the previously mentioned problems of fabrication, retention and porosity are observed.

Fumed silica - albeit not in immobilized form - has been used for the removal of hepatitis B surface antigen from fluids e.g. Stephan U.S. Pat. No. 3,686,395. Other methods of removing viruses from fluids are taught in Porath et al U.S. Pat. No. 3,925,152, Andersson et al U.S. Pat. No. 4,168,300, Wallis et al U.S. Pat. No. 3,770,625, Vnek et al U.S. Pat. No. 3,951,937 and Bick et al U.S. Pat. No. 4,057,628. None of these references uses or suggests immobilized inorganic adsorbants.

At this point it is worth mentioning commonly assigned U.S. Pat. No. 4,228,462 to Hou and Ostreicher for METHOD FOR REMOVING CATIONIC CONTAMINANTS FROM BEVERAGES, which describes a method for preparing a filter sheet having anionic electrokinetic capture potential, which cOmprises cellulose pulp, particulate filter aids, an inorganic cationic surface charge modifier and an inorganic anionic charge modifier, wherein the charge modifiers are cationic and anionic colloidal (inorganic) silicas respectively. Among the particulate aids are mentioned diatomaceous earth, perlite, talc, silica gel, etc., having a high surface area, and being preferably siliceous materials such as the finer grades of diatomaceous earth-perlite. The reason for utilizing the anionic charge modifiers, however, is so as to provide high electrokinetic capture potential for positively charged fluid contaminants. Further, the reason for using inorganic (rather than organic) charge modifiers is so as to prevent the possibility of extracting organic elements into the filtrate. No solution is offered for the production of microparticulate-containing fibrous media.

A need therefore exists for a method of homogeneously immobilizing particulate materials having millimicron sized average diameters, especially fumed silica, into fibrous matrices. A need also exists for the products produced by such method.

SUMMARY OF THE INVENTION

It is an object of the invention to provide fibrous media containing millimicron-sized particulates immobilized therein.

It is another object of the invention to provide a method for the production of fibrous media containing millimicron sized particulates immobilized therein.

Yet another object of the invention is to provide fibrous materials containing fumed silica and/or alumina immobilized therein.

Still another object of the invention is to provide a method for the production of fibrous media containing fumed silica dispersed therein.

Another object of the invention is to provide for a method of removal of HBsAg from fluids by using immobilized fumed silica, and a method of removal of pyrogens from fluids by using immobilized alumina.

These and other objects of the invention, as will hereinafter become more readily apparent have been attained by providing:

A self supporting fibrous matrix, preferably a sheet, containing immobilized therein, at least about 5% by weight of microparticulate material having an average diameter less than 1 micron, an organic polycationic resin and an organic polyanionic resin, wherein said resins are present in an amount effective to flocculate said microparticulate in said matrix.

The objects of this invention have also been attained by providing:

In a method of fabricating a self-supporting fibrous matrix containing particulate material, the improvement wherein said material has an average diameter less than 1 micron and wherein said fabrication is carried out in the presence of flocculating amounts of an organic polycationic resin and an organic polyanionic resin.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
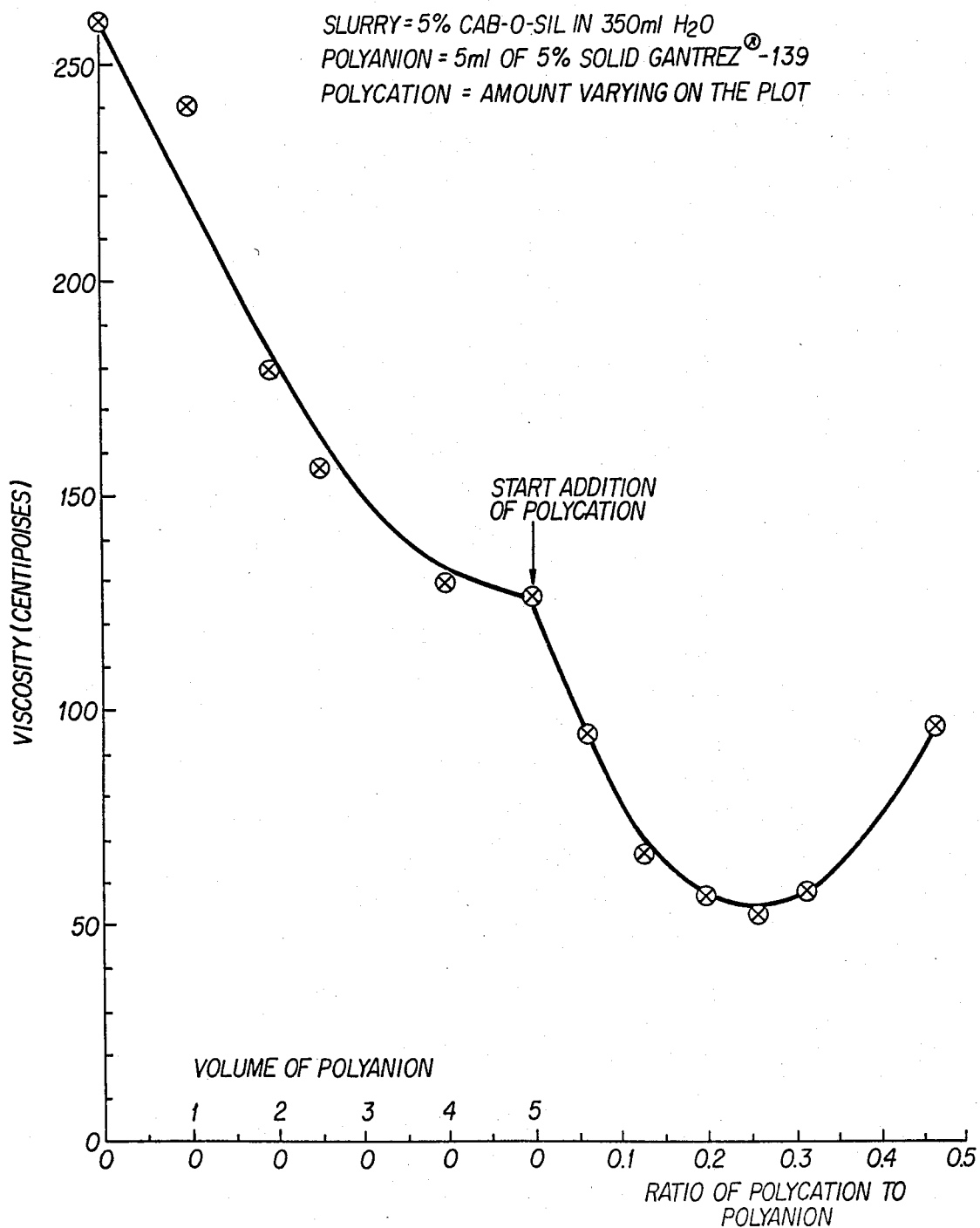
FIG. 1 shows the effect of added polyanion (G-139) on the viscosity of a 5% slurry of Cab-O-Sil ® fumed silica in water; and shows the effect of the polycation (1884)/ polyanion (G-139) resin ratio on the viscosity the same slurry.

The present invention is based on the discovery that fabrication of self-supporting fibrous media containing millimicron sized particulate material ("microparticulates") is greatly facilitated by addition to the forming slurry of two types of organic polymeric resins: One type being a polycationic resin and the other type being a polyanionic resin. Unless both types of resins are present in the slurry of fibers and microparticulate material, the microparticulate material on the one hand fails to be flocculated or on the other hand, reaches a stage where a water impermeable gel-like structure is formed, both of which prevent felting; the vacuum felting of the slurry is severely hampered, and the micro-particulates fail to be retained by the fibrous matrix. As a result of this discovery it is possible to prepare for the first time, self supporting fibrous matrices, especially fibrous sheets, containing high loads of micro-particulates, without fear of loss of micro-particulates during production, or subsequent liquid purification and filtration operations.

By "self-supporting fibrous media" is meant to include any coherent matrix of fibers which will maintain its shape and form when in the dry state, i.e., will not fall apart. In its most common form the self-supporting fibrous media is a sheet made from at least one component which is a long, self-bonding structural fiber, to give the sheet sufficient structural integrity in both the wet "as formed," and in the final dried condition, and also to allow handling during processing and suitability for the intended end use. Cellulose fibers such as wood pulp, cotton, cellulose acetate or rayon can be used. These fibers are typically relatively large, with commercially available diameters in the range of six to sixty micrometers. Wood pulp, can also be used, and has fiber diameters ranging from fifteen to twenty-five micrometers, and fiber lengths of about 0.85 to about 6.5 mm.

Other fibers which can be used include polyacrylonitrile fibers, nylon fibers or polyvinylchloride fibers. The preferred fibrous matrix of the invention is a porous self-bonding sheet of cellulose fibers.

The long self-bonding structural fibers are preferably obtained from normally dimensioned cellulose pulp such as manila hemp, jute, caroa, sisal, bleached or unbleached kraft, kozu and the like, which typically has a Canadian Standard Freeness of +400 to +800 ml. These long self-bonding fibers will constitute greater than 50% of the porous matrix, by weight, preferably about 66–90% of the porous matrix, and most preferably 75–83%.

When the amount of micro-particulate immobilized in the porous matrix is low, i.e., less than about 50% by weight of the media, it is preferred that the porous matrix be formed of a self-bonding matrix of normal cellulose pulp having a Canadian Standard Freeness of +400 to +800 ml.

In the preferred embodiment of this invention it is desirable to have a high amount of micro-particulate, i.e., greater than about 50% by weight of the medium immobilized in the porous matrix. It is thus desirable to use the invention described in copending application U.S. Ser. No. 123,467 to Hou et al filed Feb. 21, 1980, now U.S. Pat. No. 4,309,247, to maintain such high content of micro-particulate in the matrix. The entire disclosure of this application is incorporated herein by reference. Broadly, a minor portion of cellulose pulp refined to a Canadian Standard Freeness (CSF) of between about +100 and −600 ml is incorporated with a major portion of the normally dimensioned cellulose pulp (+400 to +800 ml). In particular, from about 1% to about 10% of the refined pulp and about 10% to about 30% of the normal cellulose pulp, by weight of the medium, is contained in the matrix, the remainder being the particulate. Generally, the weight ratio of unrefined to highly refined pulp will range from about 2:1 to about 10:1, preferably 3:1 to about 5:1. Such a mixture of pulps permits the increased retention of the fine particulates of the invention.

By "particulate" material is meant to include any adsorbent or particulate used in the filter art for some time such as those disclosed in the following U.S. patents, which are herein incorporated by reference: U.S. Pat. Nos. 2,143,044; 2,746,608; 3,238,056; 3,253,978; 3,591,010; 4,007,113; 4,160,059; 4,238,334; 3,669,841; 3,722,181; 3,795,313; 3,983,299; 4,029,583; 3,664,967; 4,053,565 and 4,105,426. Among the useful particulate is fumed silica, fumed alumina, microcarbon, inorganic salts, and various mixtures thereof. The particulates include those which can serve as support for further chemical modification of the particles. In the present invention at least some of the particulate material has on the average a diameter of less than 1 micron; i.e., a Gaussian distribution of particle diameters will have a maximum at less than 1 micron and is therefore termed "micro-particulate". Those sizes wherein this invention is most useful are less than 100 millimicrons, most preferred less than 50 millimicrons, especially between 1 and 25 millimicrons. In the preferred embodiment of the invention, the microparticulate is fumed silica or fumed alumina. As described previously, the term fumed silica includes materials made from the hydrolysis of $SiCl_4$ vapor in a flame of hydrogen and oxygen, and have diameters between 5 and 20 millimicrons. Fumed alumina includes aluminum oxide produced by flame hydrolysis of anhydrous aluminum chloride (e.g. Aluminum Oxide C from Degussa).

Generally the micro-particulate is present in the matrix in weights of at least about 5%, preferably 20–90% by weight, preferably about 70% by total weight. It is possible to use as immobilized particulate a mixture of microparticulate (average diameter less than 1 micron), with coarser particulate (having average diameter larger than 1 micron) in any ratio, preferably 5–95 parts by weight of micro to 95–5 parts of coarse particulate ratio; the total particulates content would then be within 5–90%, as before.

The critical aspect of the invention is the presence in the matrix of polysalts, formed by mixing organic polycationic resins with organic polyanionic resins. These polysalts flocculate the microparticulates and increase their retention in the matrix. Any organic polyanion or mixtures thereof, and polycation or mixtures thereof can be used. By "organic" is meant that the polymeric backbone is composed predominantly from carbon and hydrogen atoms, with the possible presence of other elements normally present in organic structures such as nitrogen, oxygen, sulfur and occasionally phosphorous. The common backbones are polyvinyl, polyacrylate, polymethacrylate, polyoxy, polythioxy, and the like. By "polymeric" is meant that the resin is composed of a plurality of repeating units. Typical molecular weights are 2,000–1,000,000 or more. The anionic or cationic characters of the resins are usually provided by the pendant groups. For anionic resins, as an example, carboxylic acid, sulfonic acid, phosphoric acid, or phosphonic acid groups can be used as pendant groups. For cationic resins, as an example, the ammonium group in its mono, di, tri or tetraalkyl forms (especially lower alkyl) is the most ubiquitous pendant group, although any positively charged pendant group can in principle, be used (pyridinium, quinolinium, etc.) Occasionally, some resins contain the positive charge directly along the backbone, and these can also be used.

Among the commercially available polyanionic resins which can be used, are polystyrenesulfonate (PSS, sold as Dow S21291 or Enjay RS-781); polyvinylsulfonate (made by Hercules); polyacrylic acid (sold as K702 or K714 by Goodrich); sodium polyacrylate (sold as K718); polymethylvinyl ether maleic anhydride copolymer (Gantrez AN-139 ®), or polytak RNA ® (sold by Penninsular Chemicals). Among the commercially available polycationics which can be used are polyvinyl butyltrimethyl ammonium chloride (sold as QT2781 or XD-7036 by Dow); polydiallyl dimethyl ammonium chloride (Calgon Hydroid 261); polyamine polyamide (Hercules 1884 ®) or poly-4-vinylpyridinum chloride (Ionic PP-110 ®).

The variables for the fibrous media of the invention, which have influence on the fabrication and final properties of the media are:
 (1) Type of fiber or fibers used;
 (2) Length to diameter (L/D) ratio of each type of fiber;
 (3) % weight of fiber in the mixture;
 (4) % weight of polysalt in the mixture and its ratio to microparticulates;
 (5) Ratio of polyanionic to polycationic components;
 (6) Type and % weight of microparticulate in the mixture;

(7) Type of resins utilized;
(8) Type of solution used for slurry (water, alcohol, solvent) to form the matrix, and pH thereof;
(9) Slurry additives (wetting agents, impurities, etc);
(10) Conditions of microparticulate flocculation; and
(11) Felting conditions.

The more relevant of these which have not already been described supra, will be discussed as a guide, and further details can be obtained from the Examples. However, the adjustment of the aforementioned variables as well as their interrelationships can be readily ascertained by those skilled in the art, without undue experimentation, depending on the type of utility desired for the final media.

The total amount of polysalt (polycation+polyanion) is that sufficient or effective to flocculate the micro-particulate present in the medium, but insufficient to form an impermeable gel which would prevent slurry felting. Normally the amount can be from 0.5 to 15% of the total weight of fibrous media, preferably 1 to 3%.

The ratio of polycation to polyanion can be adjusted so that the overall charge of the polysalt is positive, neutral or negative, depending on the relative proportions of one type of resin or the other. The best results are obtained when the polysalt is substantially neutral, i.e., when there are stoichiometrically equivalent amounts of both resins. The amounts can be readily determined by a simple pH titration. On the other hand, non-stoichiometric complexes can give rise to specialty media having e.g., overall positive charge (for the preferential trapping of negatively charged particles), or vice versa.

The self supporting fibrous matrix of the invention is preferably made by vacuum-felting an aqueous slurry of fibers, resins and particulate. This forms a sheet having the particulate immobilized in a porous matrix. The sheet shows a uniform high porosity, fine pore-size structure with excellent flow charcteristics and is substantially homogeneous with respect to the fiber, resins and particulate.

The vacuum felting is performed on a foraminous surface, normally a woven wire mesh which, in practice, may vary from 50 mesh to 200 mesh, with mesh openings ranging from 280 micrometers to 70 micrometers respectively. Finer meshes are unsuitable because of clogging problems and/or structural inadequacy.

The size of the openings in the foraminous vacuum felting surface, and the pore size of the cellulose fiber matrix of the formed sheet, are quite large in comparison to some or all of the dimensions of the fine fiber or particulate components required to produce the desired submicronic filter media sheet.

Application of polysalt to the micro-particulates can be performed in the following different modes:
(a) Coating of microparticles in the slurry with either polycation or polyanion, followed by flocculating the so coated microparticles with the oppositely charged polymers and repeating, if necessary; or
(b) Adding a small amount of polycation to the microparticles in the slurry first, then followed by an equivalent amount of polyanion, and repeating the sequence until sufficient polysalt is present in the slurry. This mode is preferred in order to add maximum amounts of polysalt to the system; or
(c) The least preferred mode, because of its negative effect on final porosity is mixing the polymers first, before adding to the microparticles to the slurry.

The sequence of adding the overall components to the slurry (i.e., fibers, other particulates, flocculated microparticulates) appears to be relatively unimportant, provided that the slurry is subjected to controlled hydrodynamic shear forces during the mixing process. In the "mixed fiber" embodiment, for example, the refined pulp is added to a slurry of the unrefined pulp and then the flocculated or unflocculated particulate is incorporated therein. The slurry is normally prepared at about 4% consistency and then diluted with additional water to the proper consistency required for vacuumfelting and sheet formation. This latter consistency will vary depending upon the type of equipment used to form the sheet. Typically the slurry is cast onto a foraminous surface, vacuum felted, and dried in the conventional manner. The flat, dimensionally stable sheet can be of any desired thickness and is then cut to the appropriate dimensions for each type of application.

The fibrous media of the invention containing microparticulate can be used in a myriad of applications wherever the free microparticulate would be used, with the advantage of solid phase immobilization.

In particular, the media can be utilized in all filtrations described in aforementioned copending U.S. applications Ser. No. 147,975 filed May 8, 1980; Ser. No. 164,797 filed May 30, 1980 and Ser. No. 123,467 filed Feb. 21, 1981. The media can be preferably used in the molecular separation (e.g., chromatographic) processes disclosed in copending, application to Crowder U.S. Ser. No. 287,609 filed July 28, 1981 for MOLECULAR SEPARATION COLUMN AND USE THEREOF herein incorporated by reference. The media can also be used in preparation of zero standard serum, as that disclosed in copending U.S. application Ser. No. 276,982, filed June 24, 1981 for PROCESS FOR PREPARING A ZERO STANDARD SERUM, herein incorporated by reference. A highly preferred use of fumed silica-containing media, is in the delipidization of biological fluids, such as for example of serum, disclosed in copending U.S. application Ser. No. 238,686 filed Feb. 27, 1981 for TISSUE CULTURE MEDIUM, herein incorporated by reference.

Another use for the fumed-silica containing media is in the removal of lipid enveloped viruses, for example hepatitis B surface antigen (HBsAg) from fluids, especially biological fluids, especially serum. Still another use is for removal of mycoplasma from fluids. Immobilized fumed alumina can be used for the removal pyrogens, endotoxins, and the like.

Because conventional techniques of flocculating particles in a fiber matrix by cationic polymers suffer from the limitation that the particles have to be one micron or larger, vacuum felting fails to form media with porosity adequate for filtration. Particles of millimicron sizes such as fumed silica cannot be flocculated to form a pad, due to hydrogen bonding forces exerted between the minute particles. This is especially so when the pH of the slurry is not neutral, causing possible ionization of the particles, as evidenced by increases in slurry viscosity.

The present invention provides a specific way to resolve these technical problems by adding both polycation and polyanion resins to the system.

Several advantages have been noted by the novel approach of the invention.
 (1) The proper ratio of polycation to polyanion can offset the hydrogen bonding force existing in the minute particle surfaces, enabling the particles to be flocculated out of the slurry system;
(2) The use of mixed fibers provides fine tuning and better control in addition to the positive-negative interaction;
(3) The discovery of this technology not only provides means of encapsulating any small size particles into fibrous structures, but can also speed up the production rate by cutting down on the felting time. Since the prime criteria for a high efficiency filter requires high surface area, which can be achieved by incorporating therein particles of relatively small size, this discovery offers a unique way of making high efficiency filters;
(4) The sequential addition of polycation and polyanion results in fibrous media with highly open porosity. More than 10% polysalt can be introduced into the structure without blocking the surface reactivity of the adsorbent particles. The non-stoichiometric addition of polyelectrolytes can confer on the media either cationic or anionic character, depending on the type of polyelectrolyte added in excess;
(5) The chemical nature of the polysalt complex is biocompatible and closely resembles body tissues, such as collagen. The complex is very permeable to water, which makes the material an ideal binder for filters in bio-applications;
(6) The polysalt is also a superior retention aid for the fibrous media, judging from the amount of fumed silica retained in a pad structure, and as an excellent wet strength provider shown from the testing results later described herein.

Having now generally described this invention the same will become better understood by reference to certain specific examples which are included herein for purposes of illustration only and are not intended to be limiting unless otherwise specified.

EXAMPLE 1

Preparation of Cellulose Based Media Containing Fumed Silica Particulate

I. General

Large cellulosic fibers (+400 to +800 CSF) were dispersed to a 1% solids content in a water slurry. After complete dispersion, short fibrilated cellulosic fiber (+40 to −10 CSF) was added to the slurry to a 3.5% consistency. This was followed by addition of the fumed silica (Aerosil 380 ®, 7 millimicrons), anionic polymer, silicas of relatively larger sizes (such as Sipernet 22 ®) and cationic polymer.

Sufficient agitation and mixing was allowed at every stage of addition. The mixture was pumped through a 100 mesh screen vacuum forming pot, and the filter pad was formed upon the application of vacuum to decant the water. The time required for the disappearance of water inside the pot after the application of vacuum is defined as the felting time. The smaller the particle sizes in the slurry, the longer the felting time to form the filter pad.

Table 1 shows the media made by this process, as well as the felting times.

TABLE 1

| Filter # | Fibers | | Particulate | | Resin[1] | | Felting time (min.) | Weight (g) |
|---|---|---|---|---|---|---|---|---|
| | Large Cellulosic Coho (%) | Short Micro-flake (%) | Aerosil 380 ® (%) | Sipernet 22 ®[2] (%) | Polyacrylic acid (%) | 1884 ® (%) | | |
| 1 | 20 | 10 | 50 | 20 | 0 | 2 | 11.5 | 14.7 |
| 2 | 20 | 10 | 50 | 20 | 2 | 2 | 3.0 | 15.0 |
| 3 | 20 | 10 | 50 | 20 | 4 | 2 | 4.4 | 15.5 |
| 4 | 20 | 10 | 50 | 20 | 6 | 2 | 6.5 | 16.1 |
| 5 | 20 | 10 | 50 | 20 | 8 | 2 | 7.5 | 16.6 |
| 6 | 20 | 10 | 50 | 20 | 8 | 4 | 5.0 | 17.0 |
| 7 | 20 | 10 | 50 | 20 | 0 | 4 | 20.0 | 15.2 |

[1] The amount of resin is given per 100% by weight of total fibers and total particulate, for convenience.
[2] Sipernet 22 ® is a trademark of DeGussa and represents silica having 50–70 m$\mu$ average diameter.

II. Viscosity Measurements

There is a direct relation between slurry viscosity and felting time. It is impossible to felt the slurry when it is highly viscose. The effect of ionic resin on slurry viscosity was thus measured by Brookfield viscosimetry, and expressed in centipoises (CPS) units. 5% of fumed silica (Cab-O-Sil ®) (Cabot Corporation) was dispersed in 350 ml of water.

The change of viscosity of the fumed silica slurry upon addition of Gantrez AN-139 © thereto in 5% solids concentration, is shown in FIG. 1. (Gantrez AN-139 © is a polymethyl vinyl ether and maleic anhydride copolymer from GAF Corporation). The polymer is strongly anionic in nature. The decrease in slurry viscosity indicates that the polymer perturbs the hydrogen bonding force between the fumed silica particles. The decrease of viscosity reached a plateau after 5 ml of Gantrez solution had been added.

Further reduction of slurry viscosity could only be achieved by adding to the aforementioned slurry a polycationic resin, such as polycup 1884 ® (Hercules Chemicals), as also shown in FIG. 1. Polycup 1884 ® is a high molecular weight polyamine-polyamide and epichlorohydrin copolymer, commonly used in the paper and pulp industry as a cationic flocculant. Either cationic 1884 ® or anionic Gantrez 139 ® reduced the slurry viscosity to certain level. Further addition of each only made the slurry more viscose. The combination of both, however, reduced the slurry viscosity to a minimum, which in turn reduced the required felting time for filter fabrication.

III. Felting Time Measurements

Aside from the results shown in Table 1, additional measurements were carried out. To this effect media were prepared as follows:
(a) Cellulosic fibers of different freeness were dispersed in water at 1% consistency;
(b) 0.5% of cationic polymer was added to coat the fiber surfaces;
(c) Aerosil 380 ® (7 millimicrons) was added to the slurry to be adsorbed on the positively charged fiber surfaces through charge interaction;
(d) Sipernet 22 ® (50 micron) was added as mechanical means of adjusting the media porosity;

(e) Another 0.5% of cationic polymer was added to confer the silica particles with a certain amount of charged sites; and (f) Proper ratio of anionic polymers was added to the slurry as chemical means of controlling the media porosity.

The felting time of the process can generally be controlled by three mechanisms:

a. The amount and the degree of refinement of the cellulosic fibers used in the matrix structure. Highly refined fibers can retain more microparticles in the pad, but would result in low porosity;

b. The ratio of large silica particles (Sipernet 22) to small fumed silica (Aerosil 380); and c. The total amount and the ratio of polycation to polyanion.

Figure 2:
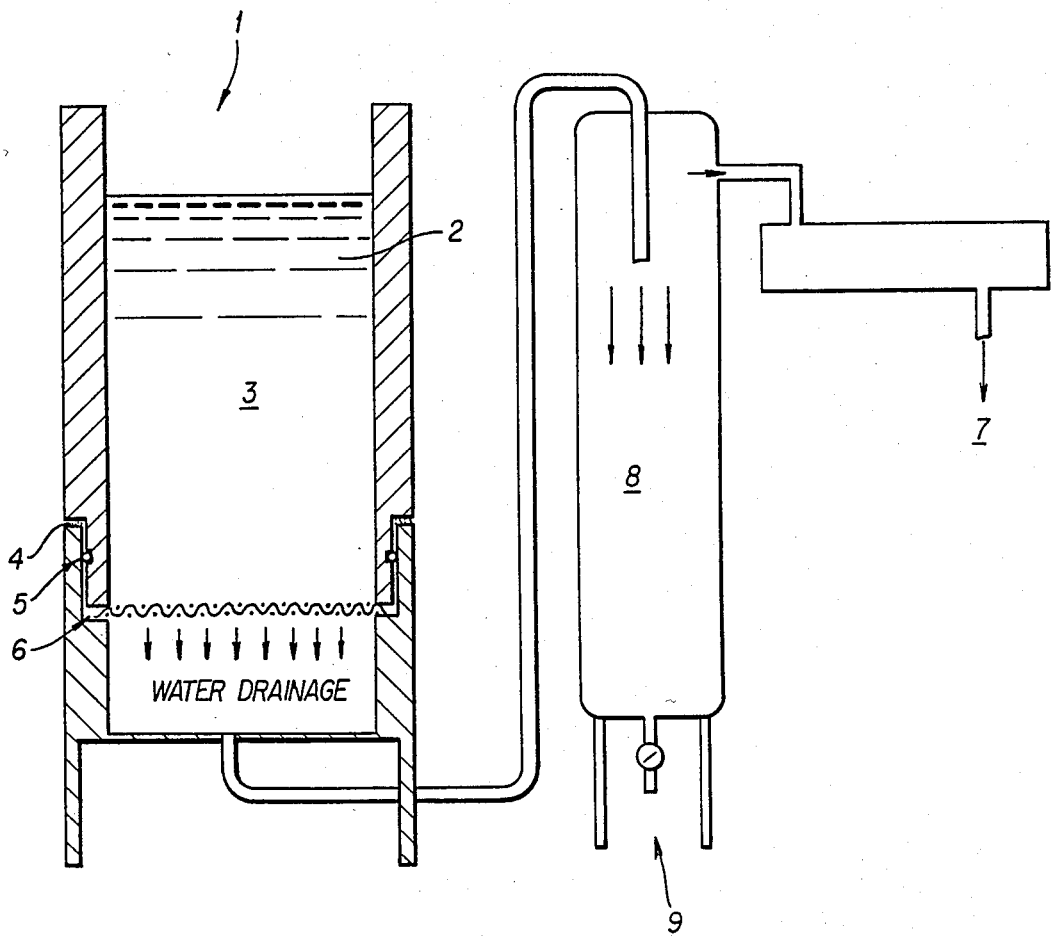
FIG. 2 shows a vacuum felting device used to measure felting times of silica-containing fiber slurries.

A device for the measurement of the felting time is shown in FIG. 2, where a filter fabricating tank 1, is shown in cross section, containing slurry 2 in container 3, which is snuggly positioned by means of rubber gasket 4, and O-ring 5 on support 6 holding a 100 mesh screen, whereupon is formed the final filter. By applying vacuum through vacuum pump 7, water from the slurry is forced through the screen and drained into drainage tank 8, where it can later be retrieved through valve 9.

The filter fabricating tank was made of a 5 inch diameter-polypropylene cylinder and a slurry containing all the components at 1% consistency was drawn through the cylinder. The length of time required to form the wet pad after applying 25 inch vacuum through the device was recorded as the felting time. For convenience and economics of production, the felting time for the filter should ideally be less than 10 minutes.

Figure 3:
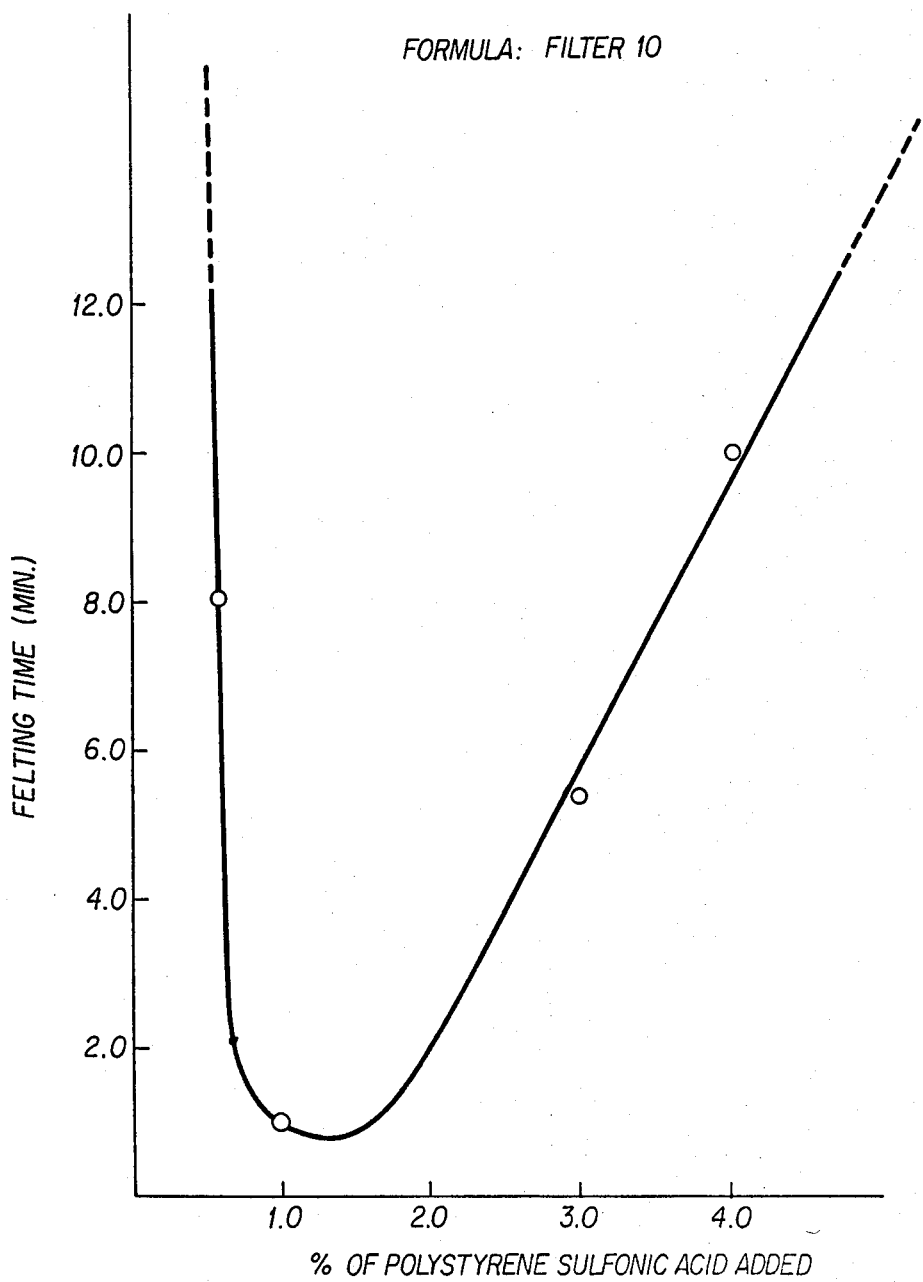
FIG. 3 shows the variation of felting time of silica-containing filter sheets containing 1% by weight polycationic resin and various amounts of polyanionic resin (polystyrenesulfonic acid, PSSA)

A polyamine polyamide (such as polycup 1884) was used as polymeric cation, and the effects of polyanion addition (such as polystyrene sulfonic acid) on the felting times of the filters are shown in Table 2 and FIG. 3.

It can be seen that the best mode of felting is with formulations having equal amounts of anion to cation (cf. filter 10). The effect of total polysalt (at a 1:1 ratio) on felting times is shown by comparing filters 10 with 13 and 14, and shows that smaller total amounts of polysalt favor shorter times. Finally, the relation of amount of Aerosil 380 to felting time can be ascertained by comparing filters 10 with filter 15 through 17.

EXAMPLE 2

Delipidization of Serum Using the Media of the Invention

I. Preliminary Evaluation of Free Silicas on Lipid Adsorptivity

Figure 4:
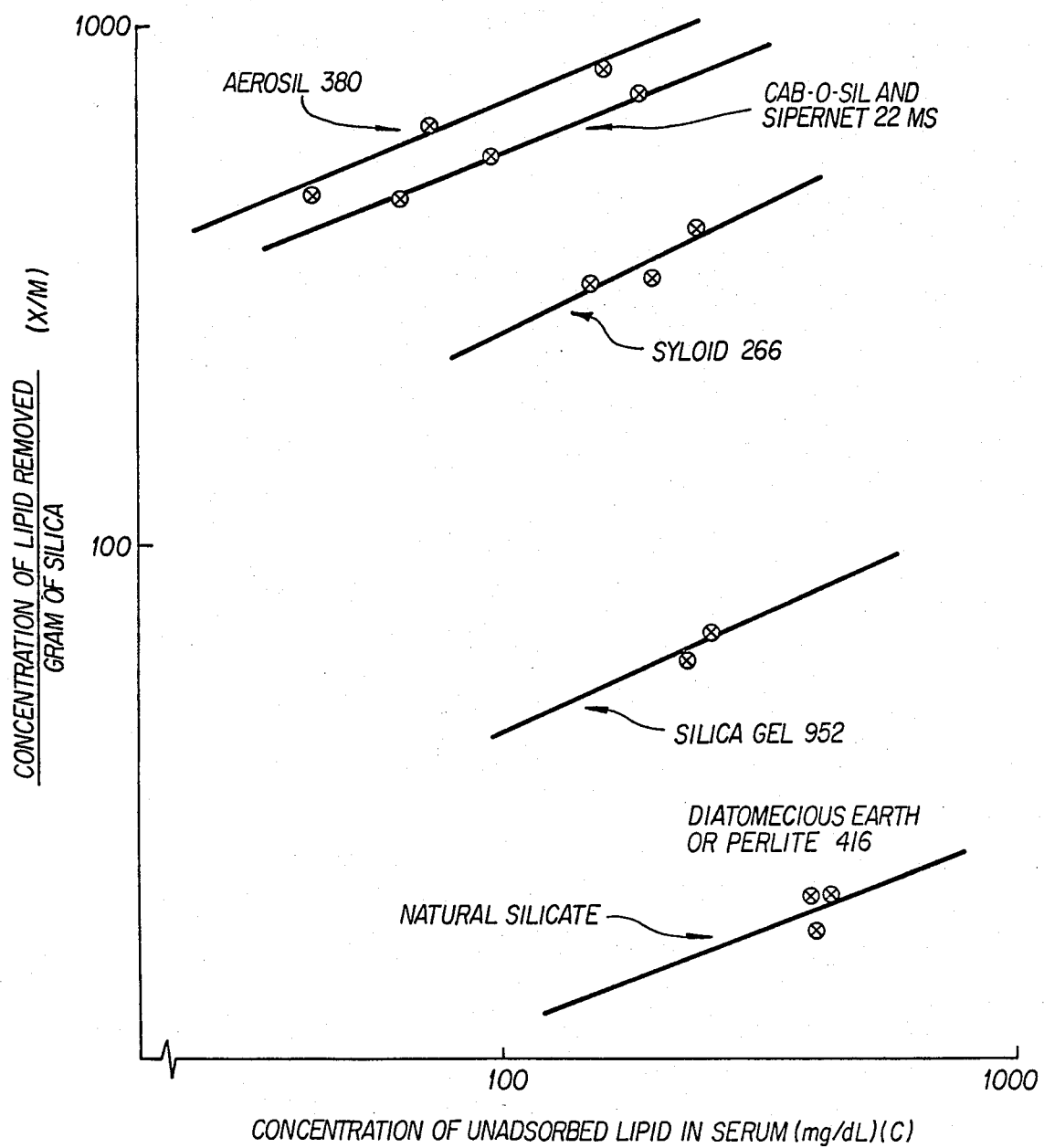
FIG. 4 shows an evaluation of delipidization of bovine serum using various different types of siliceous materials in the free state.

To ascertain what type of silica would be the best for lipid adsorption, the adsorption isotherms of lipids in bovine serum by various types of silica were studied, with the results tabulated in Table 3 and plotted in FIG. 4. The Freundlich isotherm was adopted by plotting (X/M) in milligrams of lipids per deciliter of serum adsorbed by one gram of silica vs. (C) the concentration of unadsorbed lipids remaining in the serum. The slope of the line gives the rate of change of the equilibrium relation between adsorption and lipid concentration. The amount of lipid adsorbed by unit weight of specific types of silica is a direct measure of its adsorptive capacity, which in turn gives its available number of active sites for lipid adsorption.

1. Method of Lipid Determination

The amount of lipid in bovine serum was determined by the sulfo-phospho vanillin method by measuring the (pink) color developed at a wavelength of 540 nm, with olive oil serving as a standard. The Procedure was as follows:

(1) 10 µL of $H_2O$ (blank), standard (standard), or serum (unknown), were added to 10 mL test tubes;

(2) 0.1 mL conc. $H_2SO_4$ was added to each tube and mixed;

(3) 11 tubes were placed in boiling $H_2O$ for 10 min. ($\pm 1$ min.) then cooled in cold $H_2O$ for $\simeq 5$ min;

(4) 5 mL of the phospho-vanillin reagent was added to each tube, mixed and incubated at 37° C. ($\pm 2°$ C.) in a $H_2O$ bath for 15 min;

(5) The tubes were cooled for $\simeq 5$ min. and the $A_{540}$ was measured within 30 min. (Instrument was set on blank). The reagents were as follows:

(1) Vanillin reagent: 6 g/L $H_2O$ (1 L vol. flask) (stable for 2 mo. when stored in brown bottle at room temperature);

(2) Phospho-vanillin reagent: 350 mL of vanillin reagent and 50 mL $H_2O$ to a 2 L Erlenmeyer. Add 600 mL conc. phosphoric acid with constant stirring. Store in brown bottle at room temperature;

(3) Standard: 600 mg olive oil to 100 mL vol. flask. Bring to vol. with absolute ethanol. Store at 4°–7° C.

To carry out the adsorption study, the following procedure was performed: The specific amount of silica was

TABLE 2

| | Fibers | | Particulate | | Resin[1] | | | | |
|---|---|---|---|---|---|---|---|---|---|
| Filter # | Large Cellulosic Coho (%) | Short Microflake (%) | Aerosil 380 ® (%) | Sipernet 22 ® (%) | Polycup 1884 ® acid (%) | PSSA (%) | Felting time (min.) | Weight Retained | Comments |
| 8 | 20 | 10 | 35 | 35 | 1.0 | 0.0 | ∞ | | Unable to be felted |
| 9 | 20 | 10 | 35 | 35 | 1.0 | 0.6 | 8.0 | 90% | |
| 10 | 20 | 10 | 35 | 35 | 1.0 | 1.0 | 1.0 | 91% | |
| 11 | 20 | 10 | 35 | 35 | 1.0 | 3.0 | 5.4 | 97% | |
| 12 | 20 | 10 | 35 | 35 | 1.0 | 4.0 | 10.0 | 99% | |
| 13 | 20 | 10 | 35 | 35 | 3.0 | 3.0 | 3.0 | | |
| 14 | 20 | 10 | 35 | 35 | 6.0 | 6.0 | 6.0 | | |
| 15 | 20 | 10 | 30 | 40 | 1.0 | 1.0 | 3.0 | | |
| 16 | 20 | 10 | 25 | 45 | 1.0 | 1.0 | 7.0 | | |
| 17 | 20 | 10 | 20 | 50 | 1.0 | 1.0 | 10.0 | | |
| 18 | 20 | 10 | 35 | 35 | 1.0 | 2.0[2] | 2.5 | | |

[1]The amount of resin is given per 100% by weight of total fibers and total particulate, for convenience.
[2]Polyacrylic Acid instead of PSSA.

measured accurately and added at the vortex point of 1 mL bovine serum under agitation, the tube was then incubated at 37° C. for 1 hour and centrifuged at 3000 rpm for 10 minutes to separate the adsorbent from the serum. The amount of lipid left in the serum supernatant was determined with aid of the results tabulated in Table 3.

TABLE 3

Lipid Removal from Bovine Serum by Various Types of Silica

| Nature of Silica | | M Weight of Silica Applied (in grams) | C Concentration of Unadsorbed Lipid (mg/dL) | X Concentration of Adsorbed Lipid (mg/dL) | % Lipid Removed | $\frac{X}{M}$ (mg/dL) of Lipid Adsorbed/g of silica |
|---|---|---|---|---|---|---|
| Manufacturer | Product | | | | | |
| Davidson Chemical | (size) 952 silica gel (50 micron) | 0 0.15 0.35 0.50 | 261 251 241 235 | 0 10 20 26 | 4 8 10 | 66 57 52 |
| Decalite | Perlite 416 (15 micron) | 0 0.15 0.35 0.50 | 306 303 300 298 | No effect | | 20 17 16 |
| Davidson | Syloid 266 (2 micron) | 0 0.15 0.35 0.50 | 306 246 200 151 | 0 60 106 155 | 19.6 34.7 50.6 | 400 302 310 |
| De Gussa | Aerosil 380 (7 millimicron) | 0 0.15 0.35 0.50 | 286 166 73 44 | 120 213 242 | 58.0 74.4 84.6 | 800 608 484 |
| De Gussa | Sipernet 22S (18 millimicron) | 0 0.15 0.35 0.50 | 296 188 98 66 | 108 198 230 | 36.4 66.9 77.7 | 720 565 460 |
| Cabot | M-5 (14 millimicron) | 0 0.15 0.35 0.50 | 290 200 130 59 | 90 160 231 | 31.0 55.2 79.6 | 600 457 462 |

The results indicate that natural silicas such as diatomaceous earth or perlite show no, or very little, adsorption of lipids. Silica gel is slightly better than the natural silicates. Fumed silica is far better than silica made from solution precipitation processes.

In attempting to carry out batchwise processes with fumed silica one quickly runs into serious problems. Even a small amount of fumed silica packed in a column will create extremely high pressure upon contact with buffer solutions due to the formation of a three dimensional network among the silica particles, with water molecules functioning as bridges.

Using the silica containing media of the invention, however, it is possible to overcome all of these difficulties as shown in the following study of delipidization of human serum.

II. Lipid Removal from Human Serum

Unfiltered human serum having a lipid content of 500 mg/dl was continuously filtered thrugh a plurality of filters 10 and a plurality of filters 18 (supra), and the reduction in lipid concentration is shown in Table 4, with reduction expressed as % lipid removal.

TABLE 4

| Serum Sample | Filter | No. of filters | Filter Weight (g) | Flow Rate (ml/min) | Δ P (psi) | Vol. filtered (ml) | % effective Removal |
|---|---|---|---|---|---|---|---|
| 1 | 10 | 15 | 7.2 | 1.6 | 10 | 30 | 87 |
| | | | | | | 15 | 75 |
| | | | | | | 75 | |
| | | | | | | 20 | 170 |
| | | | | | | 60 | |
| | | | | | | 25 | 300 |
| | | | | | | 40 | |
| 2 | 18 | 8 | 6.2 | 0.6 | 20 | 20 | 60 |

TABLE 4-continued

| Serum Sample | Filter | No. of filters | Filter Weight (g) | Flow Rate (ml/min) | Δ P (psi) | Vol. filtered (ml) | % effective Removal |
|---|---|---|---|---|---|---|---|
| | | | | | | 26 | 50 |
| | | | | | | 45 | |
| | | | | | | 30 | 75 |
| | | | | | | 29 | |

The results indicate that large volumes of serum can quickly and efficiently be delipidized using the filters of the present invention.

EXAMPLE 3

Pyrogen Removal by Fumed Alumina Filter

I. Fumed Alumina:

Fumed alumina with the same particle sizes as fumed silica can be produced by flame hydrolysis of anhydrous aluminum chloride. An example of such product is aluminum oxide C produced by Degussa.

II. Pyrogen Removal by Fumed Alumina Filter

Pyrogens are substances which, when injected into animals, produce fever and other reactions which can result in death. The most common pyrogenic substances are endotoxins, the lipopolysaccharide (LPS) components of gram-negative bacterial organisms. Endotoxins are pyrogens capable of producing febrile reactions in the human body after intravenous doses of as small as 1 ng/kg. The principal method for keeping parenterals free of contaminating bacterial endotoxins is to keep the manufacturing process and all subsequent handling sterile. Because maintaining sterility is difficult in many production processes, a reliable method is needed for removal of endotoxin from an accidentally contaminated product. Asbestos fiber beds can be used to remove pyrogens but their use in the United States is prohibited by Food and Drug Administration regulations.

To evaluate the performance of fumed alumina filters two types of testing procedures were used. The first involved the passage of small volumes of test solution (10–50 mL) through 0.9 cm² disc filters. The test solution was passed through the filters with the aid of a syringe at a constant flow rate. In large volume experiments usually ten liters of test solution was passed through 3.9 cm² filters at a flow rate of 3.05 gal./sq.ft./min. For contamination of the test solutions *E. coli* LPS (obtained from Sigma Chemical Company) was used. Limulus Amebocyte Lysate (LAL) for endotoxin determination was obtained from M.A. Bioproducts. Its sensitivity for endotoxin determination was evaluated for each test solution and was found to be 30 pg/mL for almost all of the test solution.

To determine endotoxin concentration, 0.1 mL lysate was mixed with 0.1 of test sample and allowed to incubate in a small test tube placed in a water bath at 37° C. for 1 hr. The formation of a gel that did not collapse upon two 180″ inversions of the tube indicated a positive test. A titration of the endotoxin was performed in every challenge to validate the sensitivity and efficiency of the LAL test.

All test samples were assayed both undiluted and at dilutions of 1:2, 1:4, 1:8, 1:16, 1:32 and 1:64, etc. The end point of each test was reached when the specimen sample showed no formation of a firm clot. This end-point dilution was then multiplied by the sensitivity of the LAL to give the approximate value of endotoxin present in the sample. Thus, concentrations of endotoxins in these studies are reported as multiples of end-point dilutions in picograms per millliter.

Procedure:

A 0.9% NaCl pH 6.7 solution for injection was contaminated with the concentration of *E. coli* endotoxin per mL indicated in Table 5 and filtered through 13 mm dia. (0.9 cm² surface area) unautoclaved filters. All filters were prewashed with 30 mL of test solution.

A filter applied for pyrogen removal is fabricated based on the formulation 10 listed in Table 2, by replacing Aerosil 380 with fumed alumina. The filter was found capable of reducing endotoxin levels to less than the limits of the assay (30 pg/mL) from small volumes when the concentration of endotoxin ranged from 1,000 to 1,000,000 pg/mL. Results are shown in Table 5.

TABLE 5

Effect on Endotoxin Concentration Removal by Fumed Alumina Filter

| Concentration of Endotoxin (pg/mL) | Endotoxin Concentration in Filtrate (pg/mL) (pg/mL) Volume passed through Filter | |
|---|---|---|
| | 10 mL | 50 mL |
| 1,000 | <30 | <30 |
| 100,000 | <30 | <30 |
| 1,000,000 | <30 | <30 |

EXAMPLE 4

Mycoplasma Removal by Fumed Silica Filter

Contamination of cell cultures by mycoplasma is a common problem in tissue culture. The fumed silica filter of the invention can remove mycoplasma very effectively, through an adsorption mechanism.

I. Test Method:

Detection of mycoplasma was performed by using a kit purchased from the Flow Laboratories, Inc., McLean, Virginia.

(a) Inoculation 10 mL of bovine serum were mixed with 40 mL broth as liquid medium. The positive controls were resuspended in 10 mL broth as standard. The liquid medium was inoculated on agar plates in 72 hours or when signs of growth appeared.

(b) Incubation

Agar plates were incubated in an inverted position in an atmosphere of 5% $CO_2$ in $N_2$ at 35° to 37° C. Additional plates may be incubated aerobically. The liquid medium was sealed and incubated aerobically. There is some question as to the usefulness of aerobic incubation. Certainly most mycoplasmas are isolated under low oxygen and increased $CO_2$ concentration.

(c) Examination of Mycoplasma Cultures

Mycoplasma colonies will frequently develop within four days of incubation but all agar plates were incubated two-three weeks before being discarded as negative.

II. Filtration procedure:

Filter 10 was cut into 25 mm diameter discs, and stacked in a plastic column with 10 filters. The bovine serum was pumped through the column at 1 mL/min. of flow with a perastaltic pump.

The filtrates were collected in the fractionation collector and inoculated on agar plates to detect mycoplasma by the Flow Lab kit as described above. The mycoplasma plaque assay was counted after two weeks of inoculation. The percentage of plaque reduction is reported as the efficiency on mycoplasma removal by the filter, in Table 6:

TABLE 6

| Filter No. | Volume of Serum filtered (mL) | Filtration Rate (mL/min) | Mean Number of Plaques | | % Plaque Reduction |
|---|---|---|---|---|---|
| | | | Influent | Effluent | |
| 10 | 10 | 1.0 | 1170 | 8 | 99.3 |
| | 20 | " | " | 10 | 99.1 |
| | 30 | " | " | 28 | 97.6 |
| | 40 | " | " | 38 | 96.7 |
| 10 | 10 | 5.0 | 550 | 80 | 85.5 |
| | 20 | " | " | 80 | " |
| | 30 | " | " | 100 | 82.0 |
| | 40 | " | " | 110 | 81.8 |
| | 50 | " | " | 140 | 75.0 |

EXAMPLE 5

Removal of Viral Hepatitis by Fumed Silica Filters

The phenomena of removal of lipids by a fumed silica filter of the invention can also be applied to the removal of virus with lipid envelopes. An example of such is the hepatitis surface antigen in human serum.

The use of fumed silica "Aerosil" ® for selective adsorption of lipoprotein from human sera has been investigated by Stephan, supra, who has recommended such treatment for the improvement of storage stability of sera in infusion. HBsAg behaves like normal serum lipoproteins and can be adsorbed very effectively on free Aerosil ®. Such treatment, however, can only be performed in small volumes of sera, since it involves high speed centrifugation to precipitate out the Aerosil ® particles.

It is also a nuisance to try to remove the traces amount of Aerosil ® left in the supernatant. A filter containing fumed silica for removing HBsAg and lipids makes the process applicable for large volume filtration with minimum protein loss.

I. HBsAg Determinations

HBsAg determinations were performed by Procedure B of Austria II-125 of Abbott Laboratories; a solid phase radioimmunoassay technique to measure HBsAg levels in serum. (See brochure of Abbott Laboratories, Diagnostics Division, entitled "Antibody to Hepatitis B Surface Antigen $^{125}$I (Human) Ausria ® II-125".) Polystyrene beads coated with guinea pig antibody are supplied in the kit. Patient serum is added and, during incubation HBsAg, if present, is fixed to the antibody. When antibody tagged with $^{125}$I is added, it binds to any HBsAg on the beads creating an antibody-antigen-antibody sandwich.

Within limits, the greater the amount of antigen in the serum specimen, the higher the final count rate.

II. Preparation of Serum Samples

Plasma from chronic carriers of HBsAg was obtained from Herman Hospital in Houston, Texas. The patients' plasma was converted to serum by calcium chloride precipitation to remove fibrinogen. Most of the serum samples showed HBsAg over 100 counts per minute which is over the sensitivity range of the Abbott Ausria kit. Dilution with 0.05 M salt phosphate buffer pH 7.2 in the range of 1:5 to 1:10 ratio will bring the counts down to the accuracy region detectable by Abbott kit. It is our general practice to keep the counts around 50-60,000 CPM, with corresponding HBsAg concentration around 0.2-0.3 microgram per mL of serum. The diluted serum was stored in a freezer to avoid the decrease of HBsAg through precipitation during the time of storage.

III. Preparation of Filter Pad

Filter No. 10 was used for the test.

IV. Experimental Set-Up

Figure 5:
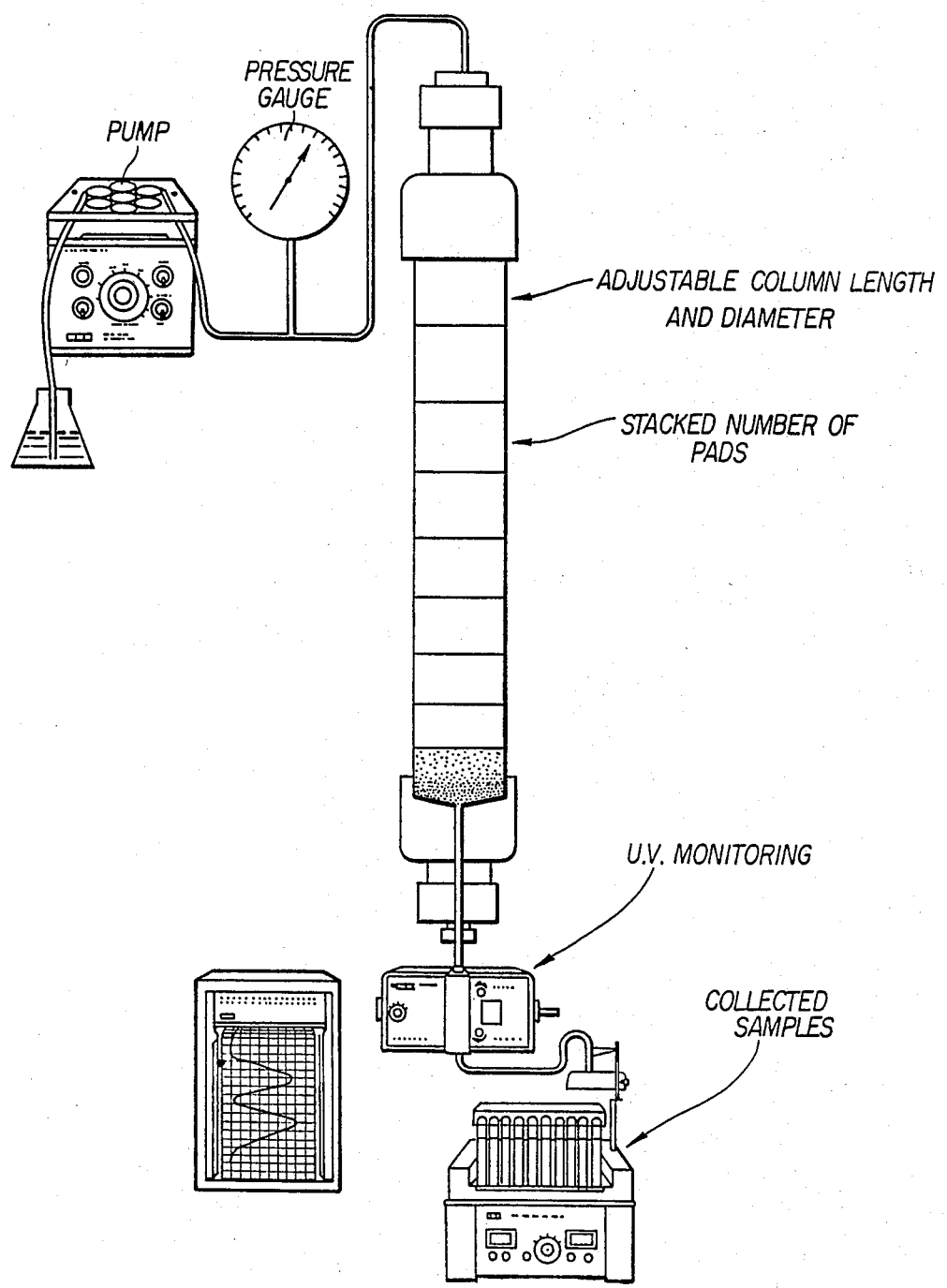
FIG. 5 shows a typical separation column using, as separation material, the fibrous media of the invention in the form of filter pads or discs.

A schematic diagram of a column for serum filtration is shown in FIG. 5. A peristaltic pump capable of handling ΔP up to 60 PSI was used. Ten filters of size 25 mm were stacked in the column. The test results were as follows:

TABLE 7

| Filter Type | Flow Rate (mL/min) | Volume of Serum filtered (mL) | Counts per Min. (CPM) Influent | Counts per Min. (CPM) Effluent | % Removal based on CPM |
|---|---|---|---|---|---|
| 10 | 2 mL/min | 10 | 2284 | 175 | 92.7 |
|  |  | 20 | " | 169 | 92.6 |
|  |  | 30 | " | 170 | 92.6 |
| 10 | 2 mL/min | 25 | 7818 | 1028 | 87.0 |
|  |  | 50 | " | 3912 | 50.0 |
|  |  | 75 | " | 5845 | 25.0 |
|  |  | 100 | " | 6659 | 15.0 |

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. A process of delipidizing a lipid-containing fluid which comprises contacting said fluid with a self supporting fibrous matrix containing immobilized therein at least about 5% by weight of a microparticulate material having an average diameter of less than 1 micron, an organic polycationic resin and an organic polyanionic resin, wherein said resins are present in an amount effective to flocculate said microparticulate material in said matrix.

2. The process of claim 1 wherein said matrix is in the form of a sheet and said lipid-containing fluid is flowed through said sheet.

3. The process of claim 1 wherein said lipids in said fluid comprise Hepatitis B Surface Antigen (HBsAg).

4. The process of claim 1, wherein the microparticulate is fumed silica.

5. The process of claim 4, wherein the fumed silica has an average particle diameter of 5 to 20 millimicrons.

6. The process of claim 5, wherein the matrix further comprises a coarse siliceous particulate having an average diameter greater than 1 micron.

7. The process of claim 6, wherein the matrix contains 5-95 parts of fumed silica to 95-5 parts of coarser siliceous particulate per 100 parts by weight of total particulate.

8. The process of claim 1, wherein the microparticulate material is fumed alumina.

9. The process of claim 8, wherein the matrix is in the form of a sheet.

10. The process of claim 8, wherein the matrix comprises one fibrous component which is unrefined cellulose pulp having a CSF of +400 to +800 ml; and another fibrous component which is highly refined cellulose pulp having a CSF of +100 to −600 ml.

11. The process of claim 10, wherein the ratio of unrefined to refined pulp is about 2:1 to about 10:1.

12. A process for depyrogenating a pyrogen-containing fluid which comprises contacting said fluid with a self supporting fibrous matrix containing immobilized therein at least about 5% by weight of a microparticulate material having an average diameter of less than 1 micron, an organic polycationic resin and an organic polyanionic resin, wherein said resins are present in an amount effective to flocculate said microparticulate material in said matrix.

13. The process of claim 12 wherein said matrix is in the form of a sheet and said pyrogen containing fluid is flowed through said sheet.

14. The process of claim 12 wherein the microparticulate material is fumed silica.

15. The process of claim 12, wherein the microparticulate is fumed alumina.

* * * * *